United States Patent [19]

Janzen et al.

[11] Patent Number: 5,705,488
[45] Date of Patent: Jan. 6, 1998

[54] INJECTABLE COMPOSITIONS FOR SOFT TISSUE AUGMENTATION

[75] Inventors: Ernst Janzen, Laren; Matthias Johannes Hoekstra, Amstelveen; Richard P. Dutrieux, Amsterdam, all of Netherlands

[73] Assignee: Datascope Investment Corp., Montvale, N.J.

[21] Appl. No.: 589,455

[22] Filed: Jan. 22, 1996

Related U.S. Application Data

[62] Division of Ser. No. 116,517, Sep. 7, 1993, Pat. No. 5,523,291.

[51] Int. Cl.⁶ .................................................. A61K 38/39
[52] U.S. Cl. ........................ 514/21; 530/353; 530/356; 424/572
[58] Field of Search .......................... 514/21; 530/353, 530/356; 424/572

[56] References Cited

U.S. PATENT DOCUMENTS

| | | | |
|---|---|---|---|
| 4,140,537 | 2/1979 | Luck et al. | 106/155 |
| 4,179,333 | 12/1979 | Braeumer et al. | 435/60 |
| 4,233,360 | 11/1980 | Luck et al. | 428/310 |
| 4,378,224 | 3/1983 | Nimni et al. | 8/94.11 |
| 4,424,208 | 1/1984 | Wallace et al. | 424/177 |
| 4,488,911 | 12/1984 | Luck et al. | 106/161 |
| 4,587,268 | 5/1986 | Pfirrmann | 514/774 |
| 4,601,896 | 7/1986 | Nugent | 424/36 |
| 4,642,117 | 2/1987 | Nguyen et al. | 623/11 |
| 4,649,147 | 3/1987 | Mueller et al. | 514/315 |
| 4,692,552 | 9/1987 | Mueller et al. | 562/475 |
| 4,776,853 | 10/1988 | Klement et al. | 623/1 X |
| 4,801,299 | 1/1989 | Brendel et al. | 623/1 |
| 4,803,075 | 2/1989 | Wallace et al. | 424/423 |
| 4,837,285 | 6/1989 | Berg et al. | 530/356 |
| 4,950,483 | 8/1990 | Ksander et al. | 424/422 |
| 4,960,423 | 10/1990 | Smith | 623/1 |
| 5,002,071 | 3/1991 | Harrell | 128/897 |
| 5,024,841 | 6/1991 | Chu et al. | 424/422 |
| 5,028,695 | 7/1991 | Eckmayer et al. | 530/356 |
| 5,110,604 | 5/1992 | Chu et al. | 424/484 |
| 5,138,030 | 8/1992 | Pachence | 530/356 |
| 5,204,382 | 4/1993 | Tonge et al. | 524/30 |
| 5,206,028 | 4/1993 | Li | 424/484 |
| 5,523,291 | 6/1996 | Janzen et al. | 514/21 |

OTHER PUBLICATIONS

Vardaxis, et al. "Chemical and Physical Properties of Collagen Implants Influence ...", J. Biomed. Res., vol. 28, pp. 1013–25 (1994).

Jorge–Herrero, et al. "Inhibition of the Calcification of Porcine Valve Tissue ...", Biomaterials, vol. 15, No. 10, pp. 815–20, 1994.

Damink, L., Thesis entitled "Structure and Properties of Crosslinked Dermal Sheep Collagen", Chap. 10, pp. 143–59 (1965).

Brochure entitled "Toothed Colloid Mill MZ", FRYMA, Jan. 1983.

Mecham, R. P. et al., "Elastin synthesis by ligamentum nuchae fibroblasts ..." J. Cell Biol., vol. 90 (2), 332–338, 1981.

"Hackh's Chemical Dictionary", cover, first sheet, p. 171 (1969).

Thomas Register of American Manufacturers, vol. 8, pp. MIL15930–MIL15931 (1990).

*Primary Examiner*—Chhaya D. Sayala
*Attorney, Agent, or Firm*—Fitzpatrick, Cella, Harper & Scinto

[57] ABSTRACT

Injectable implant compositions for soft tissue augmentation comprise elastin and collagen and a biocompatible carrier. An injectable implant composition for soft tissue augmentation is derived from the ligamentum nuchae which has been treated to remove non-collagenous and non-elastinous proteins. Methods of making an injectable implant composition for soft tissue augmentation from the ligamentum nuchae are described.

8 Claims, No Drawings

INJECTABLE COMPOSITIONS FOR SOFT TISSUE AUGMENTATION

This application is a division of application Ser. No. 08/116,517 filed Sep. 7, 1993 U.S. Pat. No. 5,523,291.

BACKGROUND OF THE INVENTION

1. Field of the Invention

The present invention relates to injectable compositions having primary utility for soft tissue augmentation.

2. Related Background

Over the years, many attempts have been made to develop injectable compositions for soft tissue augmentation, especially breast augmentation. Although in recent years the emphasis in breast augmentation has been on surgically implantable breast prostheses, injectable compositions offer the very important advantage of being able to avoid a surgical procedure.

Some of the early attempts to make injectable compositions for breast augmentation involved the use of silicone gel. However, silicone injected subcutaneously has a tendency to migrate into the surrounding tissue causing, among other problems, granulomas. Accordingly, injectable liquid gels are no longer in use.

Subsequently, injectable collagen in suspension became the composition of choice. However, natural collagen has a great tendency to be resorbed. Therefore, in order to have soft tissue augmentation that did not dissipate shortly after injection, it was found necessary to cross-link the collagen with agents such as glutaraldehyde. Cross-linking inhibits resorption. However, recently the use of glutaraldehyde cross-linked collagen has itself come under attack.

SUMMARY OF INVENTION

The present invention addresses the problems encountered in the prior art by using injectable compositions containing non-cross-linked collagen together with significant amounts of elastin. Elastin has a much lower tendency than collagen toward resorption. Moreover, it is believed that elastin attracts fibroblasts which in turn produce new native connective tissue. Thus, when a composition according to the present invention is injected subcutaneously into soft tissue, as the injected collagen is being resorbed, new native connective tissue is being generated, until a steady state situation has been achieved.

Another advantage of using elastin is that, in suspension, it has a lower viscosity and hence flows much more readily than collagen. This characteristic of elastin makes it easier to inject higher solids content compositions than is possible when using collagen alone.

As indicated above, one use for the compositions of the present invention is for breast augmentation. Another cosmetic application is as a dermal implant to remove wrinkles, primarily around the face and neck. In addition, there are medical applications as well. For example, compositions of the present invention can be used in connection with overcoming urinary incontinence. In this latter application, a composition according to the present invention would be injected into the area of the urethral sphincter.

Other possible uses for the compositions of the present invention include load-bearing tissue augmentation, for example, under a corn, and general and specific contour improvements, for example, for nose contour corrections and to correct viral pockmarks and acne scars. For load bearing tissue augmentation, the composition of the present invention would be injected between the load bearing tissue, for example the corn, and the load exerting medium, for example the bone. To alleviate skin contour defects, such as viral infection pock marks and acne scars, the composition of the present invention would be injected into the soft tissue beneath the imperfection. Similarly, to change the contour of a person's nose, the composition of the present invention would be injected into the soft tissue of the nose.

While collagen has been used previously for the above-described applications, it has generally been in the form of cross-linked collagen. Even with cross-linked collagen, however, the resorption time is often unacceptably short, especially after repeated injections. Indeed, injections of cross-linked collagen must frequently be repeated several times over a short time span before adequate augmentation can be achieved. In addition, glutaraldehyde cross-linked collagen tends to cause tissue reactions in some patients and, also, there is some concern about potential immunological problems associated with the use of collagen that has been cross-linked with glutaraldehyde. Cross-linking agents like glutaraldehyde are known to be toxic and there is concern that repeated injections of glutaraldehyde-containing compositions may produce progressively more severe immune reactions and increasingly rapid resorption. The compositions of the present invention, on the other hand, are believed to have much longer resorption times and to produce no significant immunological or tissue reaction problems.

DETAILED DESCRIPTION

It is well known that the ligamentum nuchae is made up largely of elastin, with only a relatively small amount of collagen. Indeed, more than 70% of the dry weight of this ligament is elastin. Because of the relatively high elastin content and relatively low collagen content, it is an ideal starting material to use in making an injectable composition according to the present invention.

To make a preferred injectable composition according to the present invention, the ligamentum nuchae may be cleaned using a procedure similar to that taught in U.S. Pat. No. 5,028,695, the disclosure of which is incorporated herein by reference. Generally, it is first cleaned of blood and adherent tissue. It is then chemically treated to remove the non-elastinous and non-collagenous components. The chemical treatment generally involves first treating the ligament with a strong alkali solution, then with an acid, and then with a neutralizing agent. The alkali sequence may be repeated several times if desired. Chemical treatment is followed by mechanical working to separate the elastin fibers. The separated fibers are then suspended in a suitable biocompatible carrier, for example a mixture of water and glycerin.

Although the preferred starting material is the ligamentum nuchae, other ligaments and tendons may also be used. For example, the peritoneum, omentum and other animal membranes, especially those which have significant amounts of elastin, could be used. Also, elastin and collagen from different sources could be mixed together to produce a mix having whatever proportions are deemed advantageous for a particular application. It is believed, however, that the composition should have a minimum of perhaps as little as about 10% elastin (dry weight) and might have as much as 90% or perhaps even higher of elastin.

While, as noted above, it is believed preferable not to use any cross-linking agents, there may be applications where cross-linking can be tolerated or might even be desirable. In that event, the cross-linking agent should be one which forms strong stable bonds with the collagen so that the cross-linking agent does not leach out and so that the cross-linked collagen is non-cytotoxic and does not provoke an immune or cellular response. Such cross-linking agents might include hexamethylene diisocyanate, some polyepoxy compounds, for example, polyethylene glycol diglycidyl ether, and some water soluble carbodiimides, for example, 1-ethyl-3[3-dimethyl amino propyl]carbodiimide.HCl in the presence of N-hydroxysuccinimide.

EXAMPLE

A portion of bovine ligamentum nuchae weighing about 10 kg. was soaked overnight in about 40 l of tap water at room temperature to remove adherent blood and other water soluble components. Soaking in water also assures a more or less natural degree of hydration which is believed to facilitate the subsequent chemical treatments.

After the initial soak, the ligament was washed twice for about 10 minutes each, again in tap water, before being placed in 50 l. of 4% (w/w) solution of sodium hydroxide (NaOH) in tap water. It was permitted to remain in this strongly alkaline soak for 48 hrs. at room temperature.

The alkaline soak was followed by three 10 minute washes in 50 l. of tap water and was then subjected to a second alkaline soak, this one in a 2% (w/w) solution of NaOH in tap water at room temperature for 72 hrs. There then followed three more 10 minute washes in tap water to remove the solubilized components.

After the second alkaline soak and subsequent washes, the ligament was placed in a solution of hydrochloric acid (HCl) for about 4 hrs. The HCl solution for this soak was prepared by mixing 4 l. of concentrated (37%) HCl with 36 l. of tap water. The acid soaked ligament was then washed in tap water until the pH of the water was between about 2.5 and 3.

At that point, the ligament was placed in a sodium bicarbonate (NaHCO$_3$) soak to neutralize the remaining acid. The NaHCO$_3$ soak was prepared by adding 350 gm. of NaHCO$_3$ to 50 l. of tap water. The ligament was left in this neutralizing bath overnight and then it was again washed in tap water to remove the resulting salts. Washing continued until mixing with a silver nitrate (AgNO$_3$) solution produced no precipitates.

A kolloid mill was then used to break up the natural collagen/elastin matrix and separate the elastin fibers. Acetone extractions were then used to remove the water and the fibers were then air dried in an oven at about 75° C.

Finally, 150 gm. of the dried fibers were suspended in 2 l. of a water/glycerine mixture comprised of 1 l. water and 1 l. glycerine. This suspension was then ready for use in accordance with the present invention.

It is believed that the collagen in the composition according to this present invention acts as a stimulant during the initial phase after injection. It tends to cause some mild tissue reaction and increased vascular activity. Of course, this leads to resorption, but in the process, fibroblasts, which appear to have an affinity for elastin, invade the injected composition and attach themselves to the elastin fibers. Hence, these fibroblasts lay down an organized matrix of new native connective tissue. Eventually, the injected collagen has been resorbed and all that reins is the injected elastin in a new native connective tissue structure.

It will readily become apparent to those skilled in this art that numerous modifications, alterations and changes can be made with respect to the specifics of the above description without departing from the inventive concept described herein. Accordingly, all such variants should be viewed as being within the scope of the invention as set forth in the claims below.

What is claimed is:

1. A method of treating urinary incontinence comprising the step of injecting a composition derived from animal tissue, comprising elastin and collagen and a biocompatible carrier into the area of the urethral sphincter, said tissue having been comminuted to break up the natural collagen/elastin matrix.

2. A method of breast augmentation comprising the step of injecting a composition derived from animal tissue, comprising elastin and collagen and a biocompatible carrier into the breast, said tissue having been comminuted to break up the natural collagen/elastin matrix.

3. A method of cosmetic treatment of wrinkles comprising the step of injecting a composition derived from animal tissue, comprising elastin and collagen and a biocompatible carrier into the soft tissue in or around the face, said tissue having been comminuted to break up the natural collagen/elastin matrix.

4. A method of load bearing tissue augmentation comprising the step of injecting a composition derived from animal tissue, comprising elastin and collagen and a biocompatible carrier between said load bearing tissue and a load-exerting medium, said tissue having been comminuted to break up the natural collagen/elastin matrix.

5. A method of treating acne scars or viral pock marks comprising the step of injecting a composition derived from animal tissue, comprising elastin and collagen and a biocompatible carrier into the soft tissue underlying said scar or pock mark, said tissue having been comminuted to break up the natural collagen/elastin matrix.

6. A method of changing the contours of a nose comprising the step of injecting a composition derived from animal tissue, comprising elastin and collagen and a biocompatible carrier into the soft tissue of the nose, said tissue having been comminuted to break up the natural collagen/elastin matrix.

7. A method of making an injectable implant composition derived from animal tissue, for soft tissue augmentation from ligamentum nuchae, said tissue having been comminuted to break up the natural collagen/elastin matrix, comprising the steps of washing the ligamentum nuchae in water, treating the washed ligamentum nuchae with a strong alkali solution, treating the resulting ligamentum nuchae with an acid, treating the acid-treated ligamentum nuchae with a base to neutralize the acid, mechanically working the neutralized ligamentum nuchae to separate collagen and elastin fibers, and suspending at least some of the collagen and elastin fibers in a suitable carrier.

8. A method of making an injectable implant composition derived from animal tissue for soft tissue augmentation, said tissue having been comminuted to break up the natural collagen/elastin matrix, comprising the steps of selecting tissue starting material from the group consisting of animal ligaments, tendons and membranes, washing said tissue in water, treating the washed tissue with a strong alkali solution, treating the resulting tissue with an acid, treating the acid-treated tissue with a base to neutralize the acid, mechanically working the neutralized tissue to separate elastin fibers, and suspending at least some of the elastin fibers in a suitable carrier.

\* \* \* \* \*